(12) United States Patent
Zingde et al.

(10) Patent No.: US 8,951,720 B2
(45) Date of Patent: Feb. 10, 2015

(54) MARKERS FOR TRANSFORMED EPITHELIUM AND POTENTIAL TARGETS FOR THERAPY OF CANCER OF THE GINGIVO BUCCAL COMPLEX

(75) Inventors: Surekha Mahesh Zingde, Maharashtra (IN); Rukmini Balkrishna Govekar, Maharashtra (IN); Sadhana Kannan, Maharashtra (IN); Nikhil Sureshkumar Gadewal, Maharashtra (IN); Ketayun Ardeshir Dinshaw, Maharashtra (IN); Anil Keith D'Cruz, Maharashtra (IN); Kumar Alok Pathak, Manitoba (CA); Roshan Farokh Chinoy, Maharashtra (IN); Jai Prakash Agarwal, Maharashtra (IN); Ravi Sirdeshmukh, Andhra Pradesh (IN); Curam Sreenivasacharlu Sundaram, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 1238 days.

(21) Appl. No.: 12/526,329

(22) PCT Filed: Feb. 7, 2008

(86) PCT No.: PCT/IN2008/000077
§ 371 (c)(1),
(2), (4) Date: Jul. 12, 2010

(87) PCT Pub. No.: WO2008/096374
PCT Pub. Date: Aug. 14, 2008

(65) Prior Publication Data
US 2010/0304417 A1   Dec. 2, 2010

(30) Foreign Application Priority Data
Feb. 9, 2007   (IN) .............................. 271/DEL/2007

(51) Int. Cl.
*C12Q 1/00*     (2006.01)
*G01N 33/574*   (2006.01)

(52) U.S. Cl.
CPC .............................. *G01N 33/57407* (2013.01)
USPC ................................................ 435/4; 435/26

(58) Field of Classification Search
USPC ...................................................... 435/4, 26
See application file for complete search history.

(56) References Cited

U.S. PATENT DOCUMENTS

2005/0214880 A1   9/2005   Franzmann et al.
2007/0207479 A1   9/2007   Wong et al.

OTHER PUBLICATIONS

Turhani et al. "Identification of differentially expressed, tumor-associated proteins in oral squamous cell carcinoma by proteomic analysis", Electrophoresis, Mar. 2006, 27:1417-1423.*
Inagi et al. "Treatment effects in patients with squamous cell carcinoma of the oral cavity", Acta Otolaryngol, 2002, Suppl, 547:25-29.*
Alevizos, I., et al., "Oral cancer in vivo gene expression profiling assisted by laser capture microdissection and microarray analysis", *Oncogene*, Sep. 27, 2001, pp. 6196-6204.
Chen, J., et al., "Proteomics of buccal squamous cell carcinoma: The involvement of multiple pathways in tumorigenesis", *Proteomics*, Aug. 2004, vol. 4, NR.8, pp. 2465-2475.
Lo, et al., "Identification of over-expressed proteins in oral squamous cell carcinoma (OSCC) patients by clinical proteomic analysis", Clinica Chimica Acta, Dec. 13, 2006, pp. 101-107.
Roesch-Ely, M., et al., "Proteomic analysis reveals successive aberrations in protein expression from healthy mucosa to invasive head and neck cancer", *Oncogene*, Jan. 2007, pp. 54-64.
Deshpande, M. S., et al., PD.57, "Marginal madibulectomy for gingivo-buccal complex cancers", Jan. 1, 2005, pp. 82-83.
Roesch-Ely, M., et al., Proteomic analysis reveals successive aberrations in protein expression from healthy mucosa to invasive head and neck cancer, Oncogene (3007) 26, pp. 54-64.
Parkin, D.M., et al., "Estimates of the Worldwide Incidence of Eighteen Major Cancers in 1985", Int, J. Cancer (1993) 54, pp. 594-606.
Hunter, K., et al., "Profiling early head and neck cancer", Nature Reviews, Feb. 2005, vol. 5, pp. 127-135.
Nagpal, J., et al., "Oral cancer: reviewing the present understanding of its molecular mechanism and exploring the future directions for its effective management", Oral Oncology (2003) 39, pp. 213-221.
Gires, O., et al., "Profile identification of disease-associated humoral antigens using AMIDA, a novel proteomics-based technology" CMLS, Cell Mol. Life Sci (2004) 61, pp. 1198-2107.
Sotiriou, C., et al., "Molecular profiling of head and neck tumors", Current Opinion on Oncology, 2004 16, pp. 211-214.
Baker, H., et al., "Proteome-wide analysis of head and neck squamous cell carcinomas using laser-capture microdissection and tandem mass spectrometry", Oral Oncology (2005) 41, pp. 183-199.
Patel, V., et al., "New Approaches to the Understanding of the Molecular Basis of Oral Cancer", Critical Reviews in Oral Biology & Medicine, (2001), pp. 54-63.
Schliephake, H., "Prognostic relevance of molecular markers of oral cancer—A review", Int J. Oral Maxillofac Surg, 2003, 32, pp. 233-245.
Rauch, J., et. al., "Allogenic antibody-mediated identification of head and neck cancer antigens", Biochemical and Biophysical Research Communications, (2004) 323, pp, 150-162.

* cited by examiner

*Primary Examiner* — Bin Shen
(74) *Attorney, Agent, or Firm* — Ladas & Parry LLP

(57) ABSTRACT

Systematic comparisons of samples of adjacent clinically non malignant and tumor tissue from cancer of the gingivo buccal complex obtained during surgical resection of the tumor revealed significant differences in protein expression between the cancer tissue and the adjacent clinically non malignant tissue in each patient. This study has identified a set of new proteins which can differentiate between the epithelial tissue from cancer patients which may be useful for high-through put early detection, prognosis, and potential targets for therapy.

14 Claims, 1 Drawing Sheet

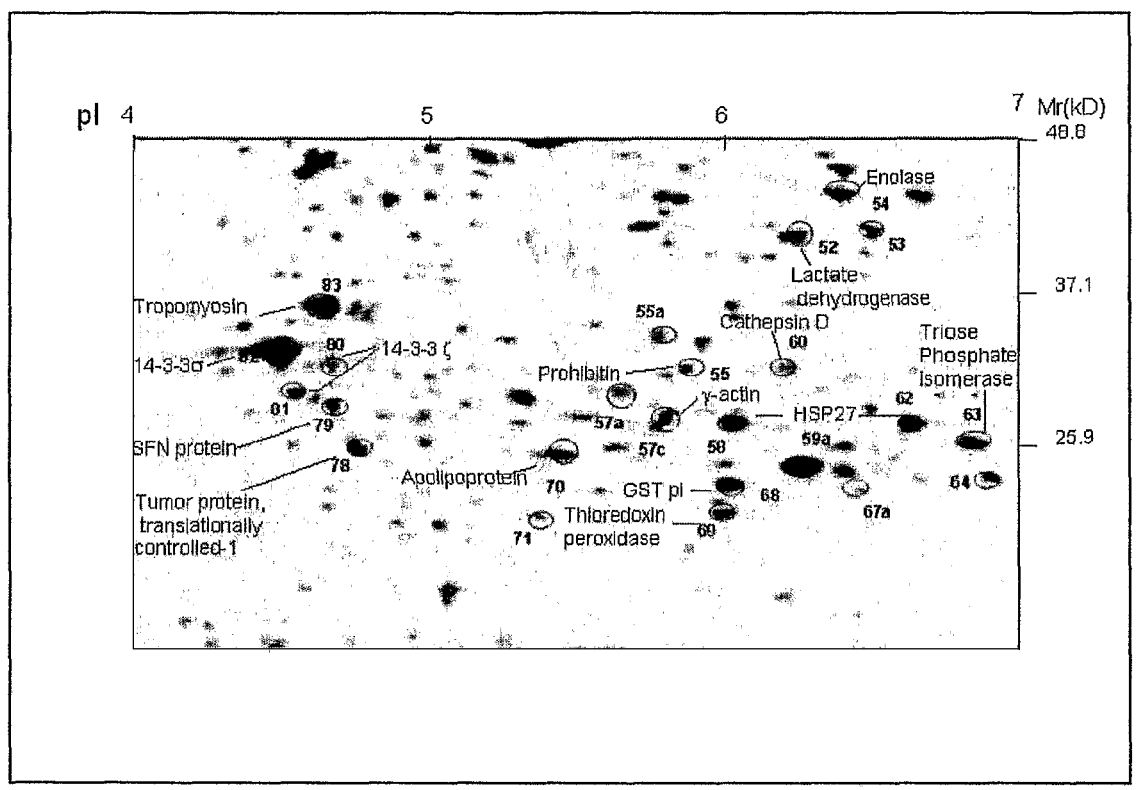

MARKERS FOR TRANSFORMED EPITHELIUM AND POTENTIAL TARGETS FOR THERAPY OF CANCER OF THE GINGIVO BUCCAL COMPLEX

This application is a 371 of PCT/IN2008/000077 filed 7 Feb. 2008, which claims priority from INDIA 271/DEL/2007 filed 9 Feb. 2007.

FIELD OF INVENTION

The present invention relates to the Identification of markers for transformed epithelium of cancer of the gingivo buccal complex which would be useful for detection, prognosis, and as potential targets for therapy.

BACKGROUND OF THE INVENTION AND PRIOR ART

Globally, oral cancer is the sixth common malignancy with about 500,000 new oral and pharyngeal cancers diagnosed annually (Parkin, Pisani, & Ferlay, 1993, Estimates of the worldwide incidence of eighteen major cancers in 1985. *Int J Cancer,* 54(4), 594-606), and three quarters of these are from the developing world. At the Tata Memorial Hospital (Dinshaw & Ganesh, 2005 *Annual Report*—2001, Hospital Based Cancer Registry, Tata Memorial Hospital), Mumbai, which registers ~30,000 cancer cases from all across the country, cancer of the oral cavity constitutes 12% of the total cancer load. Cancers of the buccal mucosa, which is a major site in the gingivo-buccal complex, are 59% of the oral cavity. Most of these cancers present at stage III and IV. The five-year survival is very low and about 60% patients return with loco-regional recurrence.

Molecular profiling of tumors is perceived as a tool for identifying prospective prognosticators or drug targets, with translational potential. For cancers of the head and neck, alterations in genes, which correlate with the now well-accepted hallmarks of cancer i.e. unregulated cell proliferation, reduced apoptosis, immortality, invasion and metastasis, and angiogenesis have been documented (Hunter, Parkinson, & Harrison, 2005 "Profiling early head and neck cancer. Nat Rev Cancer, 5(2), 127-135; Nagpal & Das, 2003 "Oral cancer: reviewing the present understanding of its molecular mechanism and exploring the future directions for its effective management". Oral Oncol, 39(3), 213-221; Patel, Leethanakul, & Gutkind, 2001 "New approaches to the understanding of the molecular basis of oral cancer" Crit. Rev Oral Biol Med, 12(1), 55-63; Schliephake, 2003 "Prognostic relevance of molecular" markers of oral cancer—a review. Int J Oral Maxillofac Surg, 32(3), 233-245; Warnakulasuriya, 2002 "In Genetics of Human Cancer, Chapter 51, 773-784). Literature reports show inconsistency in their clinical relevance (Schliephake, 2003 *"Prognostic relevance of molecular" markers of oral cancer—a review. Int J Oral Maxillofac Surg,* 32(3), 233-245). A comprehensive analysis of oral cancer microarray data in literature by Shillitoe [www.upstate.edu/microb/shillite/Microarray_Oral_Cancer Genes.HTM] shows that the irreproducibility in the alterations in mRNA expression is at 93%. Studies in both the compilations have not taken into consideration subsites of the oral cavity, differences in methodology, sample size and extent of tumor cell representation in the specimens. Even with these limitations the array data is being pursued to provide information which can be utilized for cancer management (Sotiriou, Lothaire, Dequanter, Cardoso, & Awada, 2004" Molecular profiling of head and neck tumors. *Curr Opin Oncol,* 16(3), 211-214). From these earlier studies, it is becoming increasingly apparent that identification of site-specific molecular profiles is a must for diagnosis and/or prognosis.

Proteomic analysis using two dimensional gel electrophoresis-mass spectrometry (2DE-MS) has been reported for cancer of the buccal mucosa (Chen, He, Yuen, & Chiu, 2004 "Proteomics of buccal squamous cell carcinoma: the involvement of multiple pathways in tumorigenesis. *Proteomics,* 4(8), 2465-2475), oral squamous cell carcinoma (OSCC) (Lo et al., 2007"Identification of over-expressed proteins in oral squamous cell carcinoma (OSCC) patients by clinical proteomic analysis." *Clin Chim Acta,* 376(1-2), 101-107.) and cancer of the tongue (Baker et al., 2005 "Proteome-wide analysis of head and neck squamous cell carcinomas using laser-capture microdissection and tandem mass spectrometry". Oral Oncol, 41(2), 183-199; He, Chen, Kung, Yuen, & Chiu, 2004 "Identification of tumor-associated proteins in oral tongue squamous cell carcinoma by proteomics". *Proteomics,* 4(1), 271-278). In the study with cancers of buccal mucosa (Chen et al., 2004 "Proteomics of buccal squamous cell carcinoma: the involvement of multiple pathways in tumorigenesis". *Proteomics,* 4(8), 2465-2475), the differences in protein expression between normal and tumor tissue was investigated using whole tissue samples; the tumor tissue comprising of about 70% tumor cells and normal tissue with <15% of epithelium and the rest with muscle and surrounding stroma. In the study with OSCC (Lo et al., 2007 "Identification of over-expressed proteins in oral squamous cell carcinoma (OSCC) patients by clinical proteomic analysis". *Clin Chim Acta,* 376(1-2), 101-107), the tumor tissue used contained >90% tumor cells. The percentage of normal epithelium was not defined. Baker et al (Baker et al., 2005 "Proteome-wide analysis of head and neck squamous cell carcinomas using laser-capture microdissection and tandem mass spectrometry". *Oral Oncol,* 41(2), 183-199.) have reported a protein profile for squamous cell carcinoma (SCC) of the tongue obtained after laser capture microdissection followed by LC-MS/MS analysis. The relative abundance of a protein in normal and tumor epithelium was quantified by the number of times a protein was identified in each of them. Gires et at (Gires et al., 2004 "Profile identification of disease-associated humoral antigens using AMIDA, a novel proteomics-based technology". *Cell Mol Life Sci,* 61(10), 1198-1207.) and Rauch et al (Rauch et al., 2004 "Allogenic antibody-mediated identification of head and neck cancer antigens", *Biochem Biophys Res Commun,* 323(1), 156-162.) have identified oral cancer-specific antigens eliciting immune response in patients. However, in these studies, much of the work is with tumor cell lines and head and neck tumors with no subsites defined. In none of the above studies, the relevance of the co-expression and the ability of a set of differentially expressed proteins, to distinguish between normal, benign, and transformed epithelium has been evaluated. In a very recent study (Roesch-Ely et al., 2007 "Proteomic analysis reveals successive aberrations in protein expression from healthy mucosa to invasive head and neck cancer". *Oncogene,* 26(1), 54-64.) proteomic analysis using SELDI-TOF-MS has revealed successive aberrations in protein expression from healthy mucosa to invasive head and neck cancer. In this study, however, whole tissue with tumor cells ranging from 40%-90% from different head and neck sites were used.

Our study analyses proteomic profiles of squamous cell carcinoma (SCC) of the gingivo buccal complex (GBC) and adjacent clinically non-malignant tissue from the same individuals using manually dissected epithelium. A set of differentiator proteins has been generated from relative quantitative assessment of two dimensional gel electrophoresis profiles of the dissected normal and tumor epithelia. This is the first time, for cancer of an oral subsite that co-expression of eleven proteins was found to distinguish the transformed epithelium from the normal, with good specificity and sensitivity, as assessed by cluster analysis and further confirmed with Receiver Operator Characteristics (ROC) analysis. The minimal numbers of proteins which are able to differentiate non malignant and malignant epithelial tissue were further assessed by Linear Discriminant analysis and the identity of the differentiator proteins was obtained by mass spectrometry and validated by western blotting of the total protein lysates from microdissected tissues.

Out of the proteins identified, gamma actin, HSP27, triosephosphate isomerase, GST π, 14-3-3 σ and tropomyosin were reported earlier (Chen et al., 2004 "Proteomics of buccal squamous cell carcinoma: the involvement of multiple pathways in tumorigenesis. Proteomics, 4(8), 2465-2475; Lo et al., 2007 "Identification of over-expressed proteins in oral squamous cell carcinoma (OSCC) patients by clinical proteomic analysis". *Clin Chim Acta*, 376(1-2), 101-107; Roesch-Ely et al., 2007 "Proteomic analysis reveals successive aberrations in protein expression from healthy mucosa to invasive head and neck cancer". Oncogene, 26(1), 54-64.) in oral epithelium, while lactate dehydrogenase, prohibitin, cathepsin D, thioredoxin peroxidase, apolipoprotein A-I, tumor protein translationally controlled-1, an SFN family protein and 14-3-3 ζ (YWHAZ), are being reported for the first time in the epithelium of the gingivo buccal complex by proteomic studies. The differentiators among these are lactate dehydrogenase, alpha enolase, prohibitin, cathepsin D, apolipoprotein A-I, tumor protein translationally controlled-1, an SFN family protein, 14-3-3σ tropomyosin, protein spot 81 {14-3-3ζ(YWHAZ)} and protein spot 57a for which identity is still to be obtained. Linear Discriminant analysis has additionally revealed that 14-3-3σ, lactate dehydrogenase and apolipoprotein A-I are key discriminants of the transformed epithelium and could serve as potential markers or targets for therapy.

OBJECTS OF THE INVENTION

The main object of the present invention is to provide markers for transformed epithelium and potential targets for therapy of cancer of the gingivo buccal complex. The study reports the differential protein expression in micro-dissected tumor and clinically normal tissue from the gingivo-buccal complex, by 2DE-MS approach. Co-expression of eleven proteins was found to consistently differentiate the transformed epithelium from the normal. Linear discriminant analysis further identified three of these differentiator proteins (14-3-3 sigma lactate dehydrogenase and apolipoprotein A-I) as key molecules in transformation and potential therapeutic targets. The identified differentiator proteins belong to functional pathways involved in cell transformation.

SUMMARY OF THE INVENTION

The present invention provides a system for identifying protein markers or a pattern of protein markers that indicate cancer of the gingivo buccal complex in a patient. One or more of the identified markers or the pattern of markers can then be used in diagnosis, prognosis, and/or treatment regimens related to cancer of the gingivo buccal complex. The invention involves generating a pattern of proteins in a sample using two-dimensional gel electrophoresis to identify differences between cancerous (transformed) and non cancerous (non transformed epithelium) samples from the same patient. Methods of the invention are specifically contemplated to detect cancer of gingivo buccal complex in any patient. It is contemplated that multiple cancer markers among the cancer of gingivo buccal complex proteins may be identified. At least 1, 2, 3, 4, 5, 6, 7, 8, 9, 10 or more markers of cancer of gingivo buccal complex are identified by methods of the invention. These markers may then be the direct basis for diagnosing, prognosing, or treating a patient with cancer of gingivo buccal complex.

Accordingly the present invention provides protein markers for transformed epithelium of tumor tissues of cancer of the gingivo buccal complex.

In an embodiment of the present invention the markers are lactate dehydrogenase, alpha enolase, prohibitin, cathepsin D, apolipoprotein A-I, tumor protein translationally controlled-1, an SFN family protein, 14-3-3σ, tropomyosin, 14-3-3ζ (YWHAZ).

In another embodiment of the present invention a method for identifying a set of markers for cancer of the gingiva buccal complex comprising:
  a) collecting the first sample comprising surgical specimen of tumor tissue from the gingivo-buccal area of the oral cavity of patients with cancer of the gingivo buccal complex;
  b) collecting a second sample comprising of an adjacent or contralateral clinically non malignant tissue from the gingivo-buccal area of the oral cavity of cancer patients, wherein the first and second samples comprising clinically transformed and non transformed tissue from the same cancer patient constitutes a paired sample;
  c) microdissecting the transformed epithelial cells from frozen sections of the clinically malignant tissue and the non transformed epithelial layer from frozen sections of the clinically non malignant tissue;
  d) separating proteins of the lysates prepared from microdissected transformed and non transformed epithelial cells from (c) by two-dimensional gel electrophoresis and staining with silver;
  e) comparing microdissected epithelial cell protein profiles from the samples in c) and d) to generate a short-list of protein spots commonly expressed in both normal and transformed epithelium;
  f) punching out the short listed protein gel spots from a silver stained two dimensional gel of microdissected transformed epithelial cells;
  g) destaining and drying the gel and digesting the protein with trypsin;
  h) analysing the eluted dried peptides by mass spectroscopy to obtain identities of proteins;
  i) comparing the expression of each short-listed protein spot in non malignant and transformed epithelial cells by known methods;
  j) identifying the minimal number of differentiator protein spots using Linear Discriminator Analysis.

In yet another embodiment of the present invention the identified differentiator proteins are 14-3-3σ, lactate dehydrogenase, apolipoprotein A-I.

In yet another embodiment of the present invention the proteins are useful as targets for therapy of cancer of gingivo buccal complex.

In yet another embodiment of the present invention the proteins are useful for diagnosis of cancer of gingivo buccal complex.

In yet another embodiment of the present invention the expression of the proteins are inhibited by complimentary nucleic acids, and its activity thereof by protein specific antibodies and small molecule inhibitors and similar such biomolecules either singly or in combination.

In yet another embodiment of the present invention a kit for detecting cancer of gingivo-buccal complex comprising:
  I. A set of antibodies against the antigens comprising lactate dehydrogenase, alpha enolase, prohibitin, cathepsin D, apolipoprotein A-I, tumor protein translationally controlled-1, an SFN family protein, 14-3-3 σ, tropomyosin, 14-3-3 ζ (YWHAZ),
  II. reagents capable of detecting singly or a combination of the proteins mentioned in Step a),
  III. instructions for using the kit.

In yet another embodiment of the present invention the reagents of the kit comprising:—
  A. Antibodies against the identified tumor antigens, singly or in combination, in buffered saline containing chelating agents, protease inhibitor, and non-ionic detergent.
  B. Secondary antibody tagged with biotin/horse radish peroxidase, or FITC or Cy5.
  C. Washing buffer such as buffered saline containing non-ionic detergent.
  D. Detection reagent such as streptavidin-HRP with diaminobenzidine (DAB) or only DAB or a fluorescent detector.

In yet another embodiment of the present invention use of the markers in diagnosis of cancer of gingivo-buccal complex is provided.

In yet another embodiment of the present invention use of the markers in prognosis of cancer of gingivo-buccal complex is provided.

In yet another embodiment of the present invention use of the markers as therapeutic targets for cancer of gingivo-buccal complex is provided.

In yet another embodiment of the present invention use of the kit for detection of cancer of gingivo-buccal complex in a subject is provided.

In yet another embodiment of the present invention use of the kit for prognosis of cancer of gingivo-buccal complex in a subject is provided.

In yet another embodiment of the present invention use of the proteins selected from the group consisting of lactate dehydrogenase, alpha enolase, prohibitin, cathepsin D, apolipoprotein A-I, tumor protein translationally controlled-1, a stratifin (SFN) family protein, 14-3-3σ, tropomyosin, 14-3-3ζ (YWHAZ) for screening, detection, prognosis and as potential targets for cancer of gingivo-buccal complex is established.

BRIEF DESCRIPTION OF THE DRAWINGS AND TABLES

FIG. 1, Shows a two dimensional profile of the region below 48 kD chosen for analysis and the set of potential differentiator protein spots and their identities are indicated.

Table 1A: Samples used for generating a Training set: Histology of the tissue used is given in the table. Histology of the N, adjacent normal epithelium; Nc, normal epithelium from contralateral side or CM, cut margin was either N, normal, I, inflamed or H, hyperplastic as indicated. Differentiation status of the tumor tissue section used was PD, poorly differentiated; MD, moderately differentiated; WD, well differentiated as indicated. The pathological stage of tumor is indicated. Tobacco habit, +, indicates habit of chewing tobacco, other habits of tobacco use are mentioned. Masheri is a pyrolysed tobacco product commonly used as a dentifrice. 'NA' indicates no data available. Sample numbers 415 and 618 showed nodal recurrence and distant metastasis respectively at the last follow-up, others being disease free.

Table 1B: Samples used for 2D analysis in the Test set: Histology of the tissue used is given in the table. Histology of the CM, cut margin was either N, normal, I, inflamed or H, hyperplastic as indicated. Differentiation status of the cut margins which showed involvement and the tumor tissue section used was PD, poorly differentiated; MD, moderately differentiated; WD, well differentiated as indicated. The pathological stage of tumor is indicated. Tobacco habit, +, indicates habit of chewing tobacco, other habits of tobacco use are mentioned. Masheri is a pyrolysed tobacco product commonly used as a dentifrice. Sample no, 825 showed persistent primary and nodal metastasis at the last follow-up, others being disease-free.

Table 1C: Tissues used for immunodetection by western blotting: Histology of the tissue used is given in the table. Histology of the N, adjacent normal epithelium; Nc, normal epithelium from contralateral side or CM, cut margin was either normal, I, inflamed or H, hyperplastic as indicated. Differentiation status of the cut margin which was involved or the tumor tissue section used was PD, poorly differentiated; MD, moderately differentiated; WD, well differentiated as indicated. Pathological stage of the tumor is indicated. Histology of sample numbers 457, 556, 672, 766, 788, 792, 861, 987, 988, 460, 787, 825, 828, 867 has been given in Tables 10 or 1C. Tobacco habit, +, indicates habit of chewing tobacco, other habits of tobacco use are mentioned. Masheri is a pyrolysed tobacco product commonly used as a dentifrice. 'NA' indicates no data available.

Table 1D. Histology of the samples used for IHC and IF is given in the table: Histology of the adjacent normal epithelium; Nc, normal epithelium from contralateral side or CM, cut margin was either N, normal, I, inflamed, H, hyperplastic as indicated. Differentiation status of the tumor tissue section used was PD, poorly differentiated; MD, moderately differentiated; WD, well differentiated as indicated. The pathological stage of tumor is indicated. Tobacco habit, +, indicates habit of chewing tobacco, other habits of tobacco use are mentioned. Masheri is a pyrolysed tobacco product commonly used as a dentifrice.

Table 2 shows the details of the mass spectroscopy analysis for the short-listed proteins.

Table 3 Statistical analysis of the intensities of the protein spots: The ratio of the median intensity of each of the spots from 2D gels of transformed (T) epithelium from 16 samples to the median intensity of the equivalent spot in 2D gel profiles from non transformed (N) epithelium from 14 samples in the training set is shown. The 11 spots with a ratio of the intensity greater than two or less than 0.5 and/or significantly different by Mann Whitney test are indicated by arrows. Further the Median T/N value for the 13 pairs in the samples analysed is also given for comparison. The table also shows the median T/N ratio for 17 more samples in a test set.

DETAILED DESCRIPTION

1. Protein Analysis of transformed and non transformed epithelium from tissue of the gingivo buccal complex: Since cancer of the gingivo buccal complex mainly arises due to alterations in several genes, proteomic analysis of clinically nonmalignant and malignant tissue from the oral cavity of the patient who is undergoing surgical resection for his/her tumor holds great diagnostic promise for the identification of cancer markers whose co expression pattern provides the clinician a tool for diagnosis, to assess response to therapy, recurrence, spread to nodes and survival of the patients and also potential targets for therapy. Early detection and prognosis of cancer of the gingivo buccal complex can be accomplished by analysis of non transformed epithelium and transformed epithelium from surgically resected tissues of clinically normal and cancer tissue from patient with cancer of the gingivo buccal complex. Thus, the present invention uses these tissues for detecting the development, progression and prognosis of cancer of the gingivo buccal complex comprising collecting the clinically non malignant and malignant tissue; dissecting the non transformed and transformed epithelium from frozen sections of these tissues; separating the protein in these tissues by two-dimensional gel electrophoresis; providing the protein data to a appropriate software; and analyzing the protein expression profiles. By comparing the protein profiles of the non transformed epithelium to the transformed epithelium from the same patient and/or from another patient, the present invention seeks to identify biomarkers for cancer of the gingivo buccal complex. The assay of the dissected tissues can be accomplished by two-dimensional (2D) gel electrophoresis using commercially available reagents, wherein the stained spots representing the proteins is analyzed. Staining of the proteins separated by 2D gel electrophoresis can be accomplished with colorimetric dyes (coomassie) and silver staining. In the present invention, a 2D-gel profile obtained from the transformed epithelium from the tumor tissue from a patient with cancer of the gingivo buccal complex is compared with the non transformed epithelium from the clinically normal tissue from the same patient and/or another patient, and protein losses, gains and change in expression are observed. Statistical analysis of the digitized 2D-gel profiles by the computer programs using pattern recognition methods and system can identify characteristic cancer patterns or individual protein markers that are diagnostic of cancer of the gingivo buccal complex. Protein markers of interest can then be excised from the gels using robotic technology, and the exact proteins can be identified by high-throughput matrix-assisted laser desorption ionization time of flight mass spectrometry (MALDI-Tof-Tof)-based peptide mass fingerprinting and database searching or tandem mass spectrometry sequencing of individual peptides. The amount of protein in a spot needed for identification by MALDI-Tof-Tof peptide mass fingerprint analysis of in-gel tryptic digests is roughly equivalent to the limit of detection of the protein spots by the silver stain utilized in this study. However, with pooling of the same spots from multiple gels, it is also possible to obtain enough material for tandem mass spectrometry peptide sequence analysis of relevant less abundant proteins that are detected.

II. Diagnostics, Prognostics and Therapeutics with the Identified Markers

The present invention further contemplates a method of diagnosing cancer of the gingivo buccal complex comprising the steps of collecting a first sample comprising of non malignant tissue from the buccal cavity of a patient with cancer of the gingivo buccal complex; collecting a second sample comprising malignant tissue from the buccal cavity of the same or another patient with cancer of the gingivo buccal complex, wherein the first and second samples comprising tissue from the malignant and clinically non malignant areas of the same cancer patient or another patient, wherein the cancerous tissue and the clinically non-cancerous from the same patient, constitutes a paired sample, while if they are from different patients they are sets of samples; separating the proteins by two-dimensional gel electrophoresis; and comparing the profiles of non-transformed and nontransformed epithelial proteins from the first and second sample, wherein the difference in the profiles identifies a marker for cancer of the gingivo buccal complex. In particular aspects, the sample is a tissue from the gingivo buccal cavity of a patient.

Once a cancer marker is identified, assays are employed to determine whether that marker or a combination of markers is present in a particular sample for diagnostic, prognostic, or therapeutic purposes in a cancer patient or a patient suspected of having cancer. Assays to identify a particular protein are well-known to those of ordinary skill in the art. Such assays may involve identifying a nucleic acid encoding the marker or using an antibody that specifically recognizes the marker. The diagnostic method further comprises the step of comparing the expression of the marker(s) from the cancer of the gingivo buccal complex of the invention with the expression of this marker in non-cancer samples. In more particular aspects, the comparison involves evaluating the level of expression of the marker of the cancer of the gingivo buccal complex identified herein. In further aspects, the comparison involves evaluating the structure of the gene, protein or transcript of the marker from cancer of gingivo buccal complex.

Prognostics

The markers for cancer of the gingivo buccal complex of the invention can be identified in clinically non malignant and malignant tissue from the gingivo buccal complex of a patient with cancer of the gingivo buccal complex by comparing protein profiles of each. As such, the markers from cancer of the gingivo buccal complex of the invention are useful as markers in determining whether that patient's cancer will progress and, therefore, will allow a proper determination of the need for additional therapy to be made.

The expression levels of the markers of cancer of the gingivo buccal complex of the invention, and other sequences, will also be useful in monitoring the effectiveness of a treatment regimen. In any event, the methods of the present invention will assist physicians in diagnosing cancer and in determining optimal treatment courses for individuals with tumors of varying malignancy. As described herein in detail, the amount of the markers of cancer of the gingivo buccal complex of the invention or related cancer marker present within a biological sample, such as a tissue may be determined by means of a molecular biological assay to determine the level of a nucleic acid that encodes such a polypeptide, or by means of an immunoassay to determine the level of the polypeptide itself.

It is envisioned that in clinical applications, samples of tissue from the gingivo buccal complex will be screened for the presence of the markers of cancer identified herein. Samples may also consist of punch biopsy cores, surgical resection samples or lymph node tissue. In certain embodiments, proteins would be collected from these samples and amplified as described above. Some embodiments may utilize kits containing pre-selected primer pairs or hybridization probes. The protein would be tested for the markers by any of the detection methods described herein or other suitable methods known in the art.

In other embodiments, samples of tissue from the gingivo buccal complex mucosa containing marker proteins would be collected from a patient and subjected to an immunoassay as described herein. Immunoassays of tissue sections are also possible. Kits containing the antibodies of the invention would be useful.

In terms of analyzing tissue samples, irrespective of the manner in which the level of a given cancer marker is determined, the prognostic evaluation will generally require the amount of the marker in the tissue sample to be compared to the amount in normal cells, in other patients and/or amounts at an earlier stage of treatment of the same patient. Comparing the varying levels of a given marker will allow the characteristics of the particular cancer to be more precisely defined. Thus, the co expression levels of selected markers detected, such as the markers of cancer of the gingivo buccal complex of the invention, would be compared with the markers in the nonmalignant tissue from the same patient and the differential expression would provide directions for diagnosis and prognosis of the individual patient.

Where the presence of a cancer marker correlates with cancer progression, then the clinical detection of such a marker, or an increase in the levels of such a marker, in comparison to the levels in a corresponding biological sample from a normal or even healthier subject, is indicative of a patient with advancing cancer. Likewise, where the absence of a cancer marker correlates with cancer progression, then the failure to clinically detect such a marker, or a decrease in the levels of such a marker, in comparison to the levels in a corresponding biological sample from a normal or even healthier subject, would also be indicative of a patient with advancing cancer. Those of skill in the art are very familiar with differentiating between the significant expression of a biomarker, such as the markers of cancer of the gingivo buccal complex of the invention, which represents a positive identification, and the low level or background expression of a biomarker. Indeed, background expression levels are often used to form a "cut-off" above which increased levels are scored as significant or positive. Significant expression may be represented by high levels of antigens in tissues or within body fluids, or alternatively, by a high proportion of cells from within a tissue that each gives a positive signal. If desired, the cancer screening methods of the present invention may be readily combined with other methods in order to provide an even more reliable indication of prognosis. Various markers of cancer have been proposed to be correlated with metastasis and malignancy. They are generally classified as histological, protein or nucleic acid markers. Any one or more of such methods may thus be combined with those of this invention in order to provide a multi-marker prognostic test.

Routine histological markers defining specific characteristics of the buccal mucosa tissue include such things as cellularity, nucleus to cytoplasmic ratio, disorganization of stratified epithelium, presence of keratin pearls etc. Protein markers include cytokeratins, 5, 8 and 18, actin, p53, Bcl2, Bax, Fas, Cyclin D1, alpha and beta catenin, Ki67, EGFR/p, Telomerase, NOS, Cox and Ets. All of the above markers exhibit certain drawbacks, associated with false positives and false negatives when assessed individually. A false positive result occurs when an individual without malignant cancer exhibits the presence of a "cancer marker".

A false negative result occurs when an individual actually has cancer, but the test fails to show the presence of a specific marker. The incidence of false negatives varies for each marker, and frequently also by tissue type. For example, increased expression of p53 has been reported to range from a high of 50% in head and neck cancer to a low of zero percent in the same cancers. Preferred cancer markers are those that are present in malignant cancers and either missing or else expressed at significantly lower levels in benign tumors and normal cells. As any single marker would typically be present only in some proportion of malignant cancers, it is desirable to have a number of such markers for each cancer type. The present invention addresses the need for a battery of cancer markers by identifying in clinically transformed tissue, marker(s) from cancer of the gingivo buccal complex that is expressed at higher/lower levels in malignant carcinoma than in normal tissue. In preferred embodiments, this invention provides markers for cancer of the gingivo buccal complex that are indicative of and having potential for assessing cancer progression, nodal spread, recurrence and survival. This represents a significant advance. However, combination of the present techniques with one or more other diagnostic or prognostic techniques or markers is certainly contemplated. As cancers are multifactorial, the use of more than one method or marker is often highly desirable.

B. Therapeutics: In an embodiment of the present invention, a method of treatment for cancer of buccal mucosa, by the delivery of a cancer marker protein that modulates such a cancer is contemplated. Such a therapy may be administered to a patient in an effective amount to ameliorate, reduce, minimize or limit the extent of the disease or its symptoms. More rigorous definitions may apply, including elimination, eradication or cure of disease.

C. Molecular Biological Detection Kits for Cancer of gingivobuccal complex: In some embodiments it is contemplated the aforementioned procedures of the present invention may employ the use of a kit. The materials and reagents required for detecting cancer cells in a biological sample may be assembled together in a kit. The molecular biological detection kits of the present invention, although containing at least one novel marker of cancer of the gingivo buccal complex, as disclosed herein, also may contain one or more of a variety of other cancer markers. By way of example only, one may mention other markers of cancer of buccal mucosa such as p53, bax, bcl2, EGFR, alpha catenin, Ets, Cox. Thus the markers of the gingivo buccal complex of this invention would be one of a panel of cancer markers in the kit. In further embodiments, the invention provides immunological kits for use in detecting cancer cells, e.g., in biological samples. Such kits will generally comprise one or more antibodies that have immunospecificity for proteins or peptides markers identified in this invention for cancer of the gingivo buccal complex.

As the markers for cancer of the gingivo buccal complex identified in this invention and related cancer marker proteins or peptides may be employed to detect antibodies and the anti-marker antibodies may be employed to detect cancer proteins or peptides, either or both of such components may be provided in the kit. The immunodetection kits will thus comprise, in suitable container means, the marker for cancer of the gingivo buccal complex or related cancer marker protein or peptide, or a first antibody that binds to such a cancer marker protein or peptide, and an immunodetection reagent.

Kits comprising antibodies, such as antibodies to the cancer markers for cancer of the gingivo buccal complex of the invention, will be preferred in many cases. In more preferred embodiments, it is contemplated that the antibodies will be those that bind to the epitopes of the cancer markers of the invention. Monoclonal antibodies are readily prepared and will often be preferred. Where cancer marker proteins or peptides are provided, it is generally preferred that they be highly purified.

In certain embodiments, the cancer protein or peptide, or the first antibody that binds to the marker protein or peptide, such as antibodies to the cancer markers of the gingivo buccal complex of the invention, may be bound to a solid support, such as a column matrix or well of a microtitre plate.

The immunodetection reagents of the kit may take any one of a variety of forms, including those detectable labels that are associated with, or linked to, the given antibody or antigen itself. Detectable labels that are associated with or attached to a secondary binding ligand are also contemplated. Exemplary secondary ligands are those secondary antibodies that have binding affinity for the first antibody or antigen. Further suitable immunodetection reagents for use in the present kits include the two-component reagent that comprises a secondary antibody that has binding affinity for the first antibody or antigen (generally, the antibody to the markers for cancer of the buccal mucosa of the invention or the marker peptide for cancer of buccal mucosa), along with a third antibody that has binding affinity for the second antibody, wherein the third antibody is linked to a detectable label.

As noted above in the discussion of antibody conjugates, a number of exemplary labels are known in the art and all such labels may be employed in connection with the present invention. Radiolabels, nuclear magnetic spin-resonance isotopes, fluorescent labels and enzyme tags capable of generating a colored product upon contact with an appropriate substrate are suitable examples.

The kits may contain antibody-label conjugates either in fully conjugated form, in the form of intermediates, or as separate moieties to be conjugated by the user of the kit.

The kits may further comprise a suitably aliquoted composition of the cancer protein or antigen, such as the markers for cancer of the gingivo buccal complex of the invention, whether labeled or unlabeled, as may be used to prepare a standard curve for a detection assay.

The kits of the invention, regardless of type, will generally comprise one or more containers into which the biological agents are placed and, preferably, suitably aliquoted. The components of the kits may be packaged either in aqueous media or in lyophilized form. The immunodetection kits of the invention, although containing at least one marker for cancer of the buccal mucosa antibody or antigen as identified in the present invention, also may contain one or more of a variety of other cancer marker antibodies or antigens, if so desired. Such kits could thus provide a panel of cancer markers, as may be better used in testing a variety of patients. By way of example, such additional markers could include, other tumor markers such as cytokeratins, 5, 8 and 18, actin, p53, Bcl2, Bax, Fas, Cyclin D1, alpha and beta catenin, Ki67, EGFR/p, Telomerase, NOS, Cox and Ets.

The container of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention will also typically include a means for containing the antibody, antigen, and any other reagent containers in close confinement for commercial sale. Such containers may include injection or blow-molded plastic containers into which the desired vials are retained.

EXAMPLES

The following examples are given by way of illustration of the present invention, and therefore these should not be construed to limit the scope of the present invention.

Example 1

Patients and Methods

Collection of samples:—Samples of gingivobuccal complex were collected as tumor, adjacent or contra-lateral clinically normal tissue and/or cut margin sets, from patients reporting to the Tata Memorial Hospital in Mumbai, India and diagnosed with cancer of the gingivobuccal complex. All the patients were considered candidates for curative surgical resection without prior radiotherapy or chemotherapy. Informed consent was obtained for the use of surgically resected tumor tissue and cut margins as well as for the resection of adjacent and in some cases contra-lateral mucosa. The study was approved by the Hospital Scientific Review and ethics committees of the Tata Memorial Centre. Detailed clinical information and available follow-up data were collected for subjects. All the subjects were tobacco habitú's. The samples were snap frozen in liquid nitrogen immediately upon resection and were preserved at −80° C. till use.

Antibodies and Reagents. Urea (U-5378), Thiourea (T-7875), Iodoacetamide (I-1149), Sodium Dodecyl Sulphate (L-4509), Bromophenol blue (B-5525), sequencing grade trypsin (T 6567), Diaminobenzidene (D-5637) were purchased from Sigma-Aldrich Co. USA. Tris (USB-75825), Acrylamide (USB 75820), N,N' bisacrylamide (USB 75821), Glycine (USB 16407), CHAPS (USB-13361), Dithiothreitol (US-15397), anti-mouse-HRP conjugated secondary antibody (NA 931) and the ECL (RPN 2209) and ECL plus (RPN2132) detection kits were products of Amersham Biosciences (GE Healthcare), UK. Ampholine (pH 3-10), (163-1112) and the IPG strips, pH 4-7, 7 cm (163-2001); pH 4-7, 17 cm (163-2008) were purchased from BioRad Laboratories, USA. The molecular weight Bench marker (10748-010) was a product of Invitrogen. Trifluoroacetic acid, CHCA matrix and calibration standards were from Applied Biosystems. Antibodies used for Western blotting (WB) and/or for immunohistochemistry (IHC)/immunofluorescence (IF) were from different sources as indicated: Prohibitin (Abcam ab2996), 14-3-3 σ (Upstate Biotechnology 05 632) for WB and IF, Thioredoxin peroxidase (Upstate Biotechnology 07-610), Apolipoprotein (Calbiochem 178422), GSTπ (BD Bioscience 610719), Triosephosphate isomerase (Imgenex IMG-3793), Tropomyosin (Abcam ab 7785), α-Enolase (Santacruz sc-15343), Vectastain, avidin-biotin-peroxidase complex (Vector Laboratories USA, Cat No. PK6102), rabbit anti-mouse FITC, (Sigma F9137) and goat anti-rabbit FITC (Sigma F0382). DAPI was purchased from Polysciences Inc (9224).

Processing of tissue: The quantity of adjacent/contralateral normal tissue available was generally limited. The amount of protein obtained from normal tissue after microdissection was between 23 ug-434 ug, which restricted its use to few experiments. Therefore in initial pilot experiments, samples were processed and analysed as whole tissue. Use of whole tissue allowed for several repeats when necessary. Final analyses to generate a spot set, identify differentiators and to generate training and test sets, was done with epithelium dissected from cryosectioned tissue. One section was stained with Hematoxylin and Eosin (H and E), the area of choice was marked and the other unstained sections were cut manually with a scalpel by superimposing on the stained section. Generally 50 sections were scraped for each sample. For tumor tissue 100 ug to 1 mg of protein was obtained, The whole tissue or the microdissected sections were lysed using tissue tearor (model 985370, Biospec product, Mexico) homogenizer in lysis solution containing 8 M urea, 0.2 M thiourea, 2% CHAPS, 1% dithiothreitol and 0.2% v/v ampholyte. Lysates were spun at 100,000×g for 1 h at 4° C. in a Beckman TL100 ultracentrifuge; Supernatants were aliquoted and preserved at −80° C. Protein was estimated in the supernatants by the modified Lowry's method after TCA precipitation (Peterson, 1977 "A simplification of the protein assay method of Lowry et al. which is more generally applicable". *Anal Biochem*, 83(2), 346-356).

Electrophoretic separation of proteins by 2D gel electrophoresis: Protein profiles were generated using the BioRad mini gel system using 40 µgs of whole and microdissected tissue lysates. Isoelectric focusing in the first dimension was carried out on BioRad immobiline IPG strips as described by the manufacturer. Lysates with 40 µg protein were suspended in 125 µl of the isoelectrophoresis buffer (8 M urea, 2.0 M thiourea, 2% CHAPS, 1% dithiothreitol and 0.2% ampholyte), and then overlaid on the IPG strips (7 cm, pH 4-7) and covered with 1 ml of mineral oil for rehydration overnight. The proteins were then separated in the first dimension by electrofocussing for 10,000 V-h using the BioRad IEF cell. After the isoelectrofocussing, the strips were re-equilibrated with a solution containing 2% SDS and 0.375 M Tris, pH 8.8, proteins denatured with 6 M urea, reduced with 2% DTT, alkylated with 2.5% iodoacetamide and electrophoresed on 12% SDS-polyacrylamide gels at 200 V constant voltage for 1-1.5 h until the bromophenol blue marker had reached the bottom of the gel. After electrophoresis, the proteins in the gels were visualized by staining with silver and the gel images scanned using the BioRad GS800 densitometer. For identification of protein spots by MALDI-Tof-Tof, 400 µg of the lysate proteins from the epithelial tissues were electrofocused on 17 cm strips at 40,000 V-h and the proteins were further separated in the second dimension on large gels (17 cm) at 24 mA per gel for 4-6 h.

Analysis of 2D images to obtain a 'spot-set' of commonly expressed proteins: Scanned images were analyzed and compared using the PDQuest software (version 7.1) package from BioRad. The number of spots (mean±SD) detected in the small gels were similar for normal (470±99) and tumor (532±128). In pilot studies, representative 2D profiles of proteins in whole lysates of tumor and normal tissue were analysed to obtain a pattern of spots. This was then repeated with lysates from the epithelial area of eight microdissected tumor and normal tissue pairs, no. 461, 556, 652, 671, 699, 766, 788, 792, to overcome heterogeneity arising due to inter-individual variation in protein expression and to short list proteins from epithelial tissue. Some spots excluded by the programme but expressed by more than 80% of the samples used were considered for further analysis. The union set of spots 'commonly expressed in tumor' and those 'commonly expressed in normal' epithelia yielded a short list of 21 spots which would be referred to as "spot set".

Quantitation of the intensity of the spots to obtain 'differentiators': Densitometric analysis of 2D gel profiles from microdissected normal/tumor pairs was done using image analysis software PD Quest. The intensity of each spot from the spot-set on the gel profiles was measured and normalized by dividing with the total intensity of the spots in the area under consideration as suggested by Meleth et. al (Meleth, Deshande, & Kim, 2005 "The case for well-conducted experiments to validate statistical protocols for 2D gels: different pre-processing=different lists of significant proteins. *BMC Biotechnol*, 5, 7). The fold difference in the normalized intensity of each of the short-listed spots in normal and tumor sample pairs was also obtained. The intensities of spots in the 'spot set', from normal and tumor epithelium were compared using Mann-Whitney test and those with significant differences in expression and/or with ratios greater than 2, or less than 0.5 were taken as differentiators.

Cluster Analysis. For classification of samples using markers, the data is generally divided into two-training and a test set, so as to identify and then test the markers. Likewise in the present study, the first 30 samples (T: 16; N: 14) which were collected, were used as the training set to identify the markers and these were then tested on 17 samples (T: 10; N: 7) which were collected during the later part of the study.

Generation of a training set: The normalized intensities of the spot-set from the 2D profiles of 16 tumor epithelium and 14 clinically normal sample mucosa (Table 1A) was obtained as described above. In this, thirteen 2D profiles represented sample pairs in which the tumor epithelium and clinically normal epithelium were from the same individuals. Spots which were not detected either in tumor or in normal were given a value of one as their intensity. The strength of their co-expression in terms of sample categorization was evaluated by cluster analysis. Clustering was done by calculating the Euclidean distance between samples which are then linked hierarchically by the complete linkage method using the SPSS software version 11.5.

Validation of clustering with test set: The procedure was repeated as above for 7 histologically non-transformed normal epithelium, 2 mixed epithelia; 1, (poorly differentiated, PD+ dysplastic) and 1, (hyperplastic+PD) and 8 frank tumor epithelium samples as given in Table 1B.

Tryptic digestion and mass spectrometry:—Silver stained gel plugs were destained with 100 µl of destaining solution (30 mM potassium ferricyanide/100 mM sodium thiosulfate mixed 1; 1 v/v). After thorough rinsing with water, the gel plug was dehydrated in 100% acetonitrile (ACN) which was removed by drying in a speed-vac. The proteins in the plugs were then trypsinized overnight with 15-60 ngs of trypsin in 25 mM ammonium bicarbonate in water and the peptides were recovered by extraction with 50% ACN/5% TFA. Tryptic protein digests were reconstituted in 50% ACN with 0.1% TFA solvent before subjecting them to mass analysis. The dried digests were dissolved in about 5 µL of the solvent and about 1 µl of the reconstituted digest was premixed with equal volume of CHCA matrix (α-Cyano Hydroxy Cinnamic acid), vortexed well before spotting on 384 well MALDI plate. Peptide mass finger print (PMF) data was acquired on 4800 MALDI Tof-Tof Protein Analyser (ABI, Framingham, USA) in reflector mode. Mass calibration was carried out using peptide mixture of five known peptides spanning mass range of 800-4000 m/z and was set to 10 ppm. Accelerating voltage of 20 KV was applied to the first TOF tube. The MS data was acquired in an automated manner using a solid state YAG laser at 337 nM. The resulting PMF data was processed and further analyzed using GPS software. The data was searched against NCBI database with *Homo sapiens* species using MASCOT search engine with a peptide mass tolerance of 50 ppm and S/N threshold of 10 in the mass range of 800-4000 m/z. Only those proteins identified by MASCOT search criteria with the top score were considered as acceptable. The protein Ids were examined for sequence coverage, number of peptides matched, agreement between theoretical and experimental gel MW and PI values and matching of major signals of PMF spectra with the peptides identified in the protein. The identification of protein was further confirmed by MS-MS experiment. From the PMF spectra, major intense peaks were chosen for fragmentation in the second TOF tube and MS-MS spectra were generated using high laser power. The MS-MS ions of a given peptide were searched against NCBI data base using MASCOT search engine for protein ID with precursor tolerance of 100 ppm and MS-MS fragment tolerance of 0.2 Da. Protein is considered as identified if the MS-MS ion score of individual peptide was above the threshold set by the search engine. From among the peptides submitted for searches, those with a high MS-MS ion score were chosen. In addition, combined analysis using both PMF and MS-MS data were carried out using the same criteria.

Validation of the protein identities: Commercially available antibodies were obtained for the validation of the protein identities obtained using MALDI-ToF-Tof analysis. Forty µgs of protein from the dissected epithelial lysates from normal and tumor tissue was resolved on 7 cm 2D gels and the proteins blotted on to PVDF membrane essentially according to Towbin et. al (Towbin, Staehelin, & Gordon, 1979 "Electrophoretic transfer of proteins from polyacrylamide gels to nitrocellulose sheets: procedure and some applications". *Proc Natl Acad Sci USA,* 76(9), 4350-4354) and reacted with respective antibodies (at standardized conditions). The signals for the immunoreacted protein were obtained using the corresponding secondary anti rabbit/mouse antibodies conjugated with HRP and developed with the enhanced chemiluminiscence (ECL) detection kit. The position of signal was overlapped with the stained gel to verify the position of the protein spot. Further, the protein expression data obtained in the 2DE was validated by quantitation of the signals obtained in the immunoblotting studies. For determining the relative expression of the protein in normal and transformed epithelium, protein from the lysates (1-5 µgs) from microdissected samples (Table 1C) were resolved on mini 10% or 12% 1D gels. The resolved proteins were transferred to PVDF/nitrocellulose membrane and immunostained with the respective antibodies. The intensity of the signals on the autographs was obtained using the Labworks version 4 software (UVP Bioimaging, USA). The ratio of the intensity of the band in the normal sample and the tumor tissue was obtained and normalized for equal loading by dividing with the total intensity of staining of that sample in the blot stained with colloidal gold. This was done since housekeeping proteins, like actin, show altered expression in SCC of buccal mucosa (Chen et al., 2004, Proteomics of buccal squamous cell carcinoma: the involvement of multiple pathways in tumorigenesis. *Proteomics,* 4(8), 2465-2475) which is a site included in the gingivo-buccal complex.

Immunohistochemical (IHC) and immunofluorescence (IF) staining: Confirmation of the quantitative differences observed in the 2DE and immunoblotting studies, for representative proteins with either altered expression or with no change in expression between normal and tumor, was done by quantitation of the staining obtained in tissue sections by either IHC (GST π) or IF (14-3-3 σ, prohibitin and apolipoprotein A-I). Tissues (Table 1D) embedded in paraffin blocks were cut into 5 µm thick sections. Antigens were retrieved with Tris-EDTA pH 9.0 by pressure cooker heating after quenching the inherent peroxidase activity in the deparaffinized sections with 3% hydrogen peroxide for IHC or treated with 1% Sodium borohydride for 30 mins in dark for IF. Before staining with specific antibodies, nonspecific antigenic sites were blocked with normal horse serum or normal goat serum for monoclonal and polyclonal antibodies respectively for 30 min at RT. Sections were then incubated with the respective primary antibody for 1 h at 37° C. Antibody to 14-3-3σ, GSTπ, Apolipoprotein A-I, and Prohibitin were used at a dilution of 1:50, 1:100, 1:200 and 1:50 respectively in 0.05M Tris-buffered saline pH 7.4 (TBS). This was followed by incubation with secondary biotinylated immunoglobulins (diluted 1:100) for 30 min at RT and then with avidin-biotin-peroxidase complex (1 h at RT) for IHC and the secondary FITC conjugated IgGs for IF. After each step, sections were washed with 0.05M Tris-buffered saline pH 7.4 with 0.01% Tween-20 (TBS-T). Peroxidase activity was visualized with 0.025% diaminobenzidine using 0.03% $H_2O_2$ as a substrate for IHC. Counterstaining was performed with Mayer's haematoxylin for IHC. For IF, nuclei were stained with DAPI (5 µg/ml) for 1 min. Some sections were stained in the absence of primary antibody to provide controls.

Quantitation of the immunostaining in the tissue sections: IHC was used for GSTπ and the percentage of positive cells was obtained manually by counting 100 cells in each of the 5 fields selected. For 14-3-3σ, prohibitin and apolipoprotein A-I stained by IF, the sections were scanned on the laser confocal microscope LSM 510 meta (Carl Ziess Microimaging GmbH, Germany), and fluorescence intensities of 5 fields in a 40× image from each of the sections were obtained using the image analysis software LSM 510 release 4.2 for tissue sections.

Example 2

Generation of reproducible 2D profiles and identification of a protein spot set: Scheme of the experimental design to obtain differentiators between normal and transformed tissue of the gingivo buccal complex was as follows:

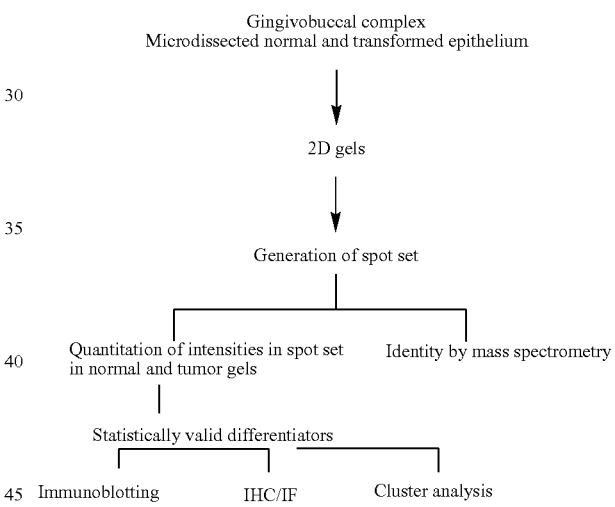

Histopathology: Table 1A, 1B 1C and 1D show the histopathological status of the samples used as microdissected tissue in the training set, test set for immunodetection on western blots and for IHC/IF respectively. In most cases the tissue dissected from the adjacent clinically normal or contralateral areas (N) and the cut margins (CM) was inflamed (I) or hyperplastic (H), while the tumor (T) was of different grades/stages.

TABLE 1A

| Sample No. | Histology of the section used from Normal(N) tissue | Histology of the section used from Cut Margin (CM) | Differentiation status of Tumor (T) tissue in section used | Pathological Stage of tumor | Tobacco habits |
|---|---|---|---|---|---|
| 356 | I | — | PD | $T_4N_0$ | + smoking |
| 358 | — | — | MD | $T_4N_0$ | Masheri |
| 415 | — | — | MD | $T_4N_1$ | + |
| 451 | — | N | WD | $T_4N_0$ | + |
| 457 | H | — | — | — | + |
| 460 | — | — | WD* | $T_4N_0$ | Smoking |

TABLE 1A-continued

| Sample No. | Histology of the section used from Normal(N) tissue | Histology of the section used from Cut Margin (CM) | Differentiation status of Tumor (T) tissue in section used | Pathological Stage of tumor | Tobacco habits |
|---|---|---|---|---|---|
| 461 | — | I | WD | $T_4N_1$ | + |
| 556 | N | — | Dysplastic | $T_3N_0$ | + |
| 618 | H, I | — | WD + MD | $T_4N_1$ | + smoking |
| 645 | — | H (mild) | WD + MD | $T_3N_0$ | + smoking |
| 652 | H | — | WD | $T_1N_0$ | + |
| 699 | I | — | MD | $T_4N_1$ | + |
| 671 | H I | — | MD | $T_4N_0$ | NA |
| 672 | H | — | WD | $T_2N_0$ | + smoking |
| 766 | I | — | MD | $T_4N_0$ | + |
| 788 | (Nc)H, I | — | WD | $T_2N_0$ | + |
| 792 | (Nc) H | — | MD | $T_4N_0$ | Smoking |

TABLE 1B

| Sample no. | Histology of tissue section used from cut margins | Differentiation Status of the Tumor (T) Tissue in the section used | Pathological stage of the tumor | Tobacco habits |
|---|---|---|---|---|
| 356 | I | — | — | + smoking |
| 457 | PD + Dysplastic | — | — | + |
| 556 | H | — | — | + |
| 652 | N | — | — | + |
| 671 | H, I | — | — | + |
| 787 | — | PD | $T_4N_{2b}$ | + |
| 825 | — | MD | $T_4N_{2b}$ | Masheri |
| 828 | — | PD | $T_4N_1$ | + |
| 861 | HI | — | — | + |
| 867 | HI | WD + PD | $T_4N_{2b}$ | + |
| 907 | — | PD | $T_2N_0$ | + |
| 923 | I | MD | $T_4N_0$ | + |
| 925 | H + PD | — | — | + |
| 987 | — | MD + dysplasia | $T_4N_0$ | + |
| 988 | — | PD | $T_4N_1$ | + |

TABLE 1C

| Sample No. | Histology of the section used from Normal(N) tissue | Histology of the section used from Cut Margin (CM) | Differentiation status of Tumor (T) tissue in section used | Pathological Stage of tumor | Tobacco habits |
|---|---|---|---|---|---|
| 161 | — | HI + T(MD) | MD | $T_2N_0$ | + |
| 365 | HI | — | PD | $T_4N_2$ | Masheri |
| 579 | HI | — | WD + PD | $T_4N_1$ | + smoking |
| 660 | N | — | WD | $T_2N_0$ | + |
| 695 | — | I | MD | $T_4N_1$ | + smoking |
| 701 | HI | — | MD | $T_4N_0$ | + |
| 763 | (Nc) N | I | PD | $T_4N_1$ | + |
| 833 | — | — | MD | $T_4N_0$ | NA |
| 321 | HI | — | MD | $T_4N_0$ | + |
| 670 | I | N | MD | $T_4N_{2c}$ | + |
| 776 | — | HI | MD | $T_4N_{2b}$ | + |
| 805 | HI | — | MD | $T_4N_{2b}$ | + smoking |
| 850 | HI | HI | MD | $T_2N_0$ | + |
| 870 | N | H | PD | $T_4N_{2b}$ | + smoking |
| 871 | N | HI | MD | $T_4N_0$ | + |
| 883 | I | HI | MD | $T_4N_0$ | + |
| 922 | HI | HI | PD | $T_4N_{2b}$ | + |
| 993 | — | I | MD | $T_4N_1$ | + |

TABLE 1D

| Sample No. | Histology of the section used from Normal(N) tissue | Histology of the section used from Cut Margin (CM) | Differentiation status of Tumor (T) tissue in section used | Pathological Stage of tumor | Tobacco habits |
|---|---|---|---|---|---|
| 1117 | HI | N | MD | T2N2b | + |
| 1116 | HI | N | MD | T4N2b | + smoking |

TABLE 1D-continued

| Sample No. | Histology of the section used from Normal(N) tissue | Histology of the section used from Cut Margin (CM) | Differentiation status of Tumor (T) tissue in section used | Pathological Stage of tumor | Tobacco habits |
|---|---|---|---|---|---|
| 1149 | HI | NI | WD | T4N0 | + |
| 1155 | NI | — | MD | T4N1 | + |
| 1167 | H | — | MD | T4N2b | + smoking |
| 1150 | NI | — | MD | T3N2b | + |
| 1158 | HI | NI | MD | T3N2b | + |
| 1133 | HI | — | PD | T2N0 | + smoking |

2D profiles and generation of a protein 'spot-set'. 2DE gel profiles of whole tissue and microdissected tumor tissue lysates were first compared to ascertain overall representation of tissue protein spots in the microdissected samples. 2DE gel profiles of the microdissected tumor tissue lysates and that of normal adjoining mucosa from eight pairs of samples were then used to generate 'spot set' as described in the methodology section. The spots identified for further analyses are shown in FIG. 1.

Example 3

Identity of the proteins in 'spot-set' by mass spectroscopy: Mass spectrometric identification was carried out for twenty one short-listed protein spots. Seventeen of them could be identified with good score (Table 2). Of these ten proteins are differentiators and one differentiator spot (57a) needs to be identified.

TABLE 2

| | | MS | | | | | | MS-MS | | |
|---|---|---|---|---|---|---|---|---|---|---|
| Spot no. | ID | Accession no. | pI | MW | Score | Sequence covera | Peptides matched (submitt | Accession no. | Peptide sequence | Total Ion score |
| 52 | Lactate dehydrogenase | gi\|49259209 | 5.86 | 36.801 | 257 | 0.57 | 24(50) | gi 4557032 | VIGSGCNIDSAR(44) GMYGIENEVFLSLPCILNAR(50) | 94 |
| 54 | Enolase 1 | gi\|62896593 | 7.01 | 47.453 | 71 | 0.29 | 9(22) | gi 3282243 | AGYTDVVIGMDVAASEFFR(20) | 20 |
| 55 | Prohibitin | gi\|4505773 | 5.57 | 29.843 | 230 | 0.6 | 16(30) | gi 30593661 | FDAGELITQR(78) KLEAEDIAYQLSR(85) | 163 |
| 57c | gamma-Actin (fragment) | gi\|178045 | 5.65 | 26.147 | 138 | 0.4 | 13(34) | gi 178045 | GYSFTTTAER(36) QEYDESGPSIVHR(101) SYELPDGQVITIGNER(73) | 210 |
| 58 | Heat shock 27 kDa protein | gi\|4504517 | 5.96 | 22.826 | 184 | 0.6 | 12(26) | gi 15126735 | RVPFSLLR(46) LFDQAFGLPR(80) LATQSNEITIPVTFESR(133) | 259 |
| 60 | Cathepsin P | gi 5822091 | 5.31 | 26.46 | 88 | 0.33 | 8(11) | gi30582659 | YYTVFDRDNNR(14) ISVNNVLPVFDNLMQQK(16) | 30 |
| 62 | Heat shock 27 kDa protein | gi\|4504517 | 5.98 | 22.826 | 134 | 0.59 | 13(50) | gi 54696638 | RVPFSLLR(47) LFDQAFGLPR(93) LATQSNEITIPVTFESR(123) | 263 |
| 63 | Triose-phosphate Isomerase | gi\|999892 | 6.51 | 26.81 | 65 | 0.49 | 12(131) | * | | |
| 68 | Glutathione-transferase PI | gi\|20664358 | 5.09 | 23.43 | 100 | 0.57 | 8(20) | gi2780952 | PPYTVVYFPVR(85) FQDGDLTLYQSNTILR(160) ALPGQLKPFETLLSONQGGK(140) | 385 |
| 69 | Thioredoxin peroxidase | gi\|9955007 | 5.44 | 21.909 | 114 | 0.34 | 8(19) | gi 33188452 | QITVNDLPVGR(60) | 60 |
| 70 | Apolipoprotein A-I | gi\|90108664 | 5.27 | 28.06 | 257 | 0.69 | 20(33) | gi 253362 | DEPPQSPWDR(47) LLDNWDSVTSTFSK(66) | 113 |
| 78 | Tumor protein, trans- | gi\|4507669 | 4.84 | 19.697 | 91 | 0.54 | 15(50) | gi 4507669 | IREIADGLCLEVEGK(34) DLISHDEMFSDIYK(71) | 105 |

TABLE 2-continued

| | | MS | | | | | MS-MS | | |
|---|---|---|---|---|---|---|---|---|---|
| Spot no. | ID | Accession no. | pI | MW | Sequence Score | Peptides covera matched (submitt | Accession no. | Peptide sequence | Total Ion score |
| | lationally-controlled 1 | | | | | | | | |
| 79 | SFN protein | gi\|49456765 | 4.64 | 27.874 | 97 | 0.54 | 10(36) | gi 49456765 EMPPTNPIR(29) | 29 |
| 80 | YWHAZ protein | gi\|49119653 | 4.72 | 30.1 | 115 | 0.4 | 10(30) | gi 27807367 SVTEQGAELSNEER(37) GIVDQSQQAYQEAFEISKK(92) SVTEQGAELSNEERNLLSVAYK(66 | 195 |
| 81 | YWHAZ protein (Tyr3/tryp5 mono-oxygenase activation protein) | gi\|4507953 | 4.75 | 27.72 | 135 | 0.441 | 13 | ** | |
| 82 | Stratifin | gi\|5454052 | 4.68 | 27.871 | 88 | 0.35 | 6(13) | gi 631131 LGLALNFSVFHYEIANSPEEAISLAK (117) | 117 |
| 83 | Tropomyosin 3 | gi\|10901654 | 4.79 | 29.109 | 149 | 0.44 | 15(43) | gi 55665780 EQAEAEVASLNRR(56) IQLVEEELDRAQER(60) | 116 |

*no MS-MS data
**no MS-MS data MS data obtained on MALDI microMX, Waters.

The pattern of protein spots from the epithelial cells used for the analysis and their identities are shown in FIG. 1 and Table 2. Identities of 8 proteins, viz prohibitin, HSP27, triose phosphate isomerase, GST π, thioredoxin peroxidase, apolipoprotein A-I, 14-3-3 σ and tropomyosin, were further confirmed with immunostaining of the 2D gels with specific antibodies.

Example 4

Quantitative analysis of the 'spot-set' on 2D profiles of microdissected non-transformed and tumor epithelial tissue: A training set (Table 1A) of seventeen patients with cancer of the gingivo buccal complex, were analyzed for quantitation of the short-listed spots. The malignant tumor tissue (n=16) and the adjacent clinically non-malignant tissue (n=14) were manually microdissected and two-dimensional electrophoretic profiles generated as described. Of these 30 samples, 26 were paired samples (13 pairs). The intensity of spots in the spot-set, in these samples was compared and evaluated statistically to obtain the differentiators and were further analyzed by cluster analysis to generate a 'training set'. A 'test set' (Table 1B) of 17 samples was analyzed as above to validate the results from the training set in cluster analysis. Together, the data on quantitation of 2D profiles of normal and transformed epithelial tissue and mass spectrometric analysis of the short-listed proteins reveals that: Proteins alpha enolase, gamma actin, HSP27, triosephosphate isomerase, GSTπ, 14-3-3 σ and tropomyosin have been reported earlier (Chen et al., 2004 "; Proteomics of buccal squamous cell carcinoma: the involvement of multiple pathways in tumorigenesis. Proteomics, 4(8), 2465-2475. Lo et al., 2007" Identification of over-expressed proteins in oral squamous cell carcinoma (OSCC) patients by clinical proteomic analysis. Clin Chim Acta, 376(1-2), 101-107; Roesch-Ely et al., 2007 "Proteomic analysis reveals successive aberrations in protein expression from healthy mucosa to invasive head and neck cancer". Oncogene, 26(1), 54-64.) in oral epithelium, while lactate dehydrogenase, prohibitin, cathepsin D, thioredoxin peroxidase, apolipoprotein A-I, tumor protein translationally controlled-1 and an SFN family protein and 14-3-3 ζ (YWHAZ), have not been reported from normal and transformed epithelium of the gingivo buccal complex by proteomic studies. The differentiators among these are lactate dehydrogenase, alpha enolase, prohibitin, cathepsin D, apolipoprotein A-I, tumor protein translationally controlled-1, an SFN family protein, 14-3-3σ tropomyosin, protein spot 81{14-3-3ζ(YWHAZ)} and protein spot 57a for which identity is still to be obtained. Linear Discriminant analysis has additionally revealed that 14-3-3σ, lactate dehydrogenase and apolipoprotein A-I are key discriminants of the transformed epithelium and could serve as potential markers or targets for therapy.

Statistical and Cluster Analysis:

Training set—The difference in the intensities of each of the spots from the 30 samples in the training set was subjected to the Mann Whitney analysis and the data is given in Table 3. The median T/median N ratios of the protein spots 52, 54, 55, 78, 79, 82, 83 and 57a is more than 2, while that for spot 70 is less than 0.5 and the ratios for the protein spots 52, 54, 60, 70, 78, 79, 81, 82, and 57a are statistically significant by Mann Whitney analysis. This indicates the differences in expression of each of these eleven protein spots (52, 54, 55, 60, 70, 78, 79, 81, 82, 83 and 57a) which are able to distinguish clinically malignant from clinically non-malignant tissue and therefore are 'differentiators'. The T/N ratio of the median values of each of the spots from the 13 sample pairs from this set are also given in Table 3. It is seen that the trend remains the same as for the 30 samples.

TABLE 3

| | | | TRAINING SET | | | | | TEST SET | | |
|---|---|---|---|---|---|---|---|---|---|---|
| | | | 30 Gels | | | | | 17 gels | | |
| | | | Median | | 13 Ratio Pairs | | Median | | Median | |
| Spot | Median N | Median T | T/Median N | p value | T/N | p value | N (CM) | Median T | T/Median N | p value |
| → 52 | 21.07 | 65.47 | 3.11 | 0.001 | 2.43 | 0.001 | 60.70 | 97.865 | 1.61 | 0.054 |
| → 54 | 17.24 | 43.81 | 2.54 | 0.006 | 3.01 | 0.004 | 27.41 | 97.05 | 3.54 | 0.007 |
| → 55 | 15.99 | 34.68 | 2.17 | 0.114 | 1.62 | 0.228 | 42.68 | 69.295 | 1.62 | 0.083 |
| 58 | 98.03 | 108.65 | 1.11 | 0.406 | 1.06 | 0.739 | 78.00 | 152.22 | 1.95 | 0.083 |
| → 60 | 19.14 | 27.03 | 1.41 | 0.020 | 2.91 | 0.038 | 23.17 | 113.665 | 4.91 | 0.009 |
| 62 | 55.08 | 92.31 | 1.68 | 0.212 | 1.39 | 0.489 | 120.33 | 208.01 | 1.73 | 0.034 |
| 63 | 43.18 | 37.95 | 0.88 | 1.000 | 1.27 | 0.739 | 116.86 | 70.17 | 0.60 | 0.360 |
| 64 | 21.38 | 31.58 | 1.48 | 0.647 | 1.59 | 0.397 | 19.80 | 45.695 | 2.31 | 0.005 |
| 68 | 142.41 | 140.26 | 0.98 | 0.367 | 0.80 | 0.663 | 149.35 | 194.745 | 1.30 | 0.178 |
| 69 | 53.83 | 68.77 | 1.28 | 0.506 | 1.29 | 0.778 | 78.00 | 94.965 | 1.22 | 0.501 |
| → 70 | 191.84 | 90.81 | 0.47 | 0.016 | 0.49 | 0.026 | 238.51 | 153.72 | 0.64 | 0.386 |
| 71 | 25.50 | 29.14 | 1.14 | 0.835 | 0.80 | 0.663 | 31.79 | 52.62 | 1.66 | 0.009 |
| → 78 | 32.48 | 70.94 | 2.18 | 0.000 | 2.13 | 0.001 | 40.17 | 114.465 | 2.85 | 0.007 |
| → 79 | 2.04 | 25.19 | 12.38 | 0.027 | 4.59 | 0.026 | 5.12 | 12.12 | 2.37 | 0.149 |
| 80 | 23.38 | 31.49 | 1.35 | 0.280 | 1.03 | 0.343 | 61.73 | 117.69 | 1.91 | 0.005 |
| → 81 | 23.00 | 37.38 | 1.63 | 0.004 | 1.49 | 0.006 | 28.69 | 77.915 | 2.72 | 0.001 |
| → 82 | 190.27 | 439.47 | 2.31 | 0.000 | 2.50 | 0.001 | 180.04 | 522.81 | 2.30 | 0.016 |
| → 83 | 17.08 | 48.23 | 2.82 | 0.244 | 1.79 | 0.293 | 47.00 | 194.175 | 4.13 | 0.001 |
| → 57a | 31.15 | 63.93 | 2.05 | 0.016 | 1.37 | 0.026 | 25.08 | 60.305 | 2.40 | 0.124 |
| 57c | 40.39 | 58.03 | 1.44 | 0.212 | 1.42 | 0.209 | 167.66 | 68.685 | 0.41 | 0.386 |
| 59a | 54.34 | 87.30 | 1.61 | 0.406 | 1.32 | 0.317 | 26.51 | 29.52 | 1.11 | 0.630 |

The data was subjected to Receiver Operator Characteristics (ROC) analysis (Altman & Bland, 1994, "Diagnostic tests 3: receiver operating characteristic plots." *Bmj*, 309 (6948), 188) in addition to Mann Whitney test to investigate the extent to which the expression of a protein differs among individuals who do or do not have the disease of interest. A global assessment of the performance of the marker (called as discrimination accuracy) is given by the area under the curve (AUC). This area is equal to the probability that a random individual with a disease will have a higher expression for a particular marker than a random individual without the disease. No marker will be clinically useful if it cannot discriminate, so a global assessment is an important step. Also a ROC plot is particularly useful when comparing two or more markers.

Based on the global assessment, i.e., AUC the markers could be grouped into good (AUC≥0.8) moderate (0.6<AUC<80) and poor (<0.6). Thus a total of five good (78, 82, 52, 81, 54), nine moderate (70, 57a, 60, 79, 55, 57c, 62, 83, 80) and seven poor (58, 59a, 69, 64, 71, 63, 68) were identified. It is seen from Table 3 that the 11 protein spots identified by Mann Whitney analysis are also above the diagonal in the ROC assessment.

To determine if the intensity of expression of the spots on the 2D profiles could cluster into patterns, the spot intensities were used with the relevant statistical software. The strategy employed to achieve the same was as follows. Hierarchical cluster analysis was carried out for the 21 spots from 16 tumor epithelia and 14 normal samples.

Clustering of the samples was also tested with the 11 spots (52, 54, 55, 60, 70, 78, 79, 81, 82, 83 and 57a) which have a T/N value greater than 2 or less than 0.5 and are significant by Mann Whitney analysis. It is evident that these protein spots are able to segregate the samples into normal and transformed epithelium with the sensitivity of 63% and specificity of 93%.

Linear Discriminant Analysis of the data with 21 or 11 spots from the 30 samples identifies protein spots 82 (14-3-3σ) and 52 (LDH) as the key molecules which can differentiate transformed epithelium at 5% alpha and protein spot 70 i.e., Apolipoprotein A-I at 10% alpha. These molecules could be considered as potential targets for therapy.

The possible coordinated role of these identified differentiators in transformation was assessed by evaluating their association with molecules reported in literature to be differentially expressed in oral tumors and compiled in our data base and using the String Search Tool for retrieval of interacting genes/proteins as well as relevant literature. The interaction network of the 'differentiator' proteins indicates their key role in the major physiological pathways of cell proliferation, apoptosis and glycolysis which are aberrant in tumors, thereby confirming their utility as potential targets for therapeutic intervention.

Test Set. The validity of the 11 spots identified in the training set was assessed with the test set consisting of 17 sample gels detailed in Table 1B. The Mann Whitney analysis of the intensities of the 17 samples is given in Table 3. It is apparent that the trend seen in the training set continues to hold in the test set. This is further supported by the ROC analysis. It is evident from cluster analysis that 11 protein spots are able to differentiate transformed epithelium and the significance of 82 and 52 in cluster formation is confirmed. It is to be noted that the samples used in the Test Set do not represent normal and tumor tissue pairs from the same individuals unlike the situation in the Training set. Even then the 11 discriminator spots are able to segregate transformed and non transformed epithelium. The results thus support the strength of the analysis in generating a set of discriminator proteins.

The "differentiator" proteins identified in our study could be used to assess the status of the adjacent histologically normal tissue to determine if alterations are seen. If they are present, then there is need for stricter follow up or more aggressive treatment. The validation of these proteins as markers of prognosis would require information through patient follow-up. The patients are being followed-up (for a period ranging from 2-34 months) and to date fourteen out of seventeen patients from the training set, for whom follow-up data is available have not shown any recurrence of disease while one (no. 415) has shown nodal recurrence and one (no. 618) has distant metastasis. In the test set, of the eight patients follow up data was available for four and of these one (825) has shown recurrence of primary with nodal metastasis. Prospective follow-up data from these patients could, throw light on the correlation of each tumor subcluster with disease prognosis. We could also assess the ability of these markers, along with other already reported molecules, to sub classify the tumors.

Example 5

Validation of 'Differentiator' Protein Spots

Relative expression of select spots by immunostaining: The differential expression of the spots indicated by 2D patterns was confirmed by immuno-staining of select number of spots whose identity was determined by MALDI-Tof-Tof analysis and for which suitable antibodies were available. For this analysis 14 sample pairs are same as those used for 2D analysis in the training and test sets. In addition, 18 new samples (Table 1C) have been used for immunostaining. The median expression of 14-3-3 σ and prohibitin is increased in tumor tissue. This increase is significant at p=0.012 and p=0.003 for 14-3-3 σ and prohibitin respectively. The median expression of GST π is not changed while that for apolipoprotein is significantly reduced (p=0.019) in tumor tissue. The increase in levels of 14-3-3 σ and prohibitin and decrease in median expression of apolipoprotein is as seen by the quantitative Mann Whitney analysis of the 2D profiles given in Table 3 thereby confirming the observations.

Protein expression and pathological status:—The immunostaining data was evaluated vis a vis tumor grade and pathological stage. Majority of the samples were at the T4 stage. Only prohibitin exhibited a correlation between the level of expression and pathological stage ($N_0$ vs N+). Prohibitin levels were increased nearly 4-fold in node-positive versus node-negative samples (2.28 vs 0.54; p=0.08).

Immunohistochemistry (IHC) or immunofluorescence staining (IF): IF or IHC was done to confirm the information obtained by 2D and immunoblotting. Immunofluorescence was done for evaluating the expression of 14-3-3 σ and prohibitin which are increased in tumor, and apolipoprotein A-I which is decreased in tumor, as all these three antigens are located in the cytosol/nucleus or membrane, thereby necessitating a more automated quantitation. IHC was done for GST π whose levels are unaltered between normal and tumor samples by 2D and western blotting and is seen only in the nucleus by IHC enabling manual quantification. It is apparent that each of these antigens are detected in distinct subcellular locales. 14-3-3 σ is seen in the nucleus/perinuclear region/cytosol in the tissues. Prohibitin is perinuclear and lightly cytosolic in both normal and tumor tissue sections with more cells showing perinuclear staining in the tumor sample sections. Apolipoprotein was seen as expressed in the suprabasal layer in the normal tissues and was detected around the cell membrane in sections from both normal and tumor samples, the staining being discontinuous in the tumor tissue. GST π is essentially nuclear in normal and tumor with expression in both basal and suprabasal layers. Eight pairs (Table 1D) of histologically normal and tumor tissue sections were stained for the antigens 14-3-3 σ and prohibitin using immunofluorescence. In parallel with the observations in 2D and western blot analysis, a significant increase in levels of 14-3-3 σ (median T/N ratio of 1.98; p=0.002) and prohibitin (median T/N ratio of 1.56; p=0.001) was observed.

For apolipoprotein the median T/N ratio was 1.08 and the difference between normal and tumor was not significant unlike that observed by 2D and western blotting. For GST π the levels as quantitated by 2D and western blotting are unaltered in tumor as compared to normal and the same is seen when assessed by IHC. The median of percentage positive cells in normal tissue sections was 90.6 while that in tumor tissue were 95.3. The difference between the two is insignificant. The data on immunoblotting, immunohisto- and cytochemical detection confirms the differentiators in formats routinely used in diagnostic laboratories and therefore validate their use for molecular diagnostics.

ADVANTAGES

1. It is believed that a new application of proteomic analysis of microdissected epithelium from cancer of the gingivo buccal complex has identified for the first time, a battery of markers whose co-expression pattern could achieve segregation of normal and transformed epithelium.
2. The invention involves the identification of potential targets for therapy of cancer of the gingivo buccal complex.
3. The interaction network of the 'differentiator' proteins indicates their key role in the major physiological pathways of cell proliferation, apoptosis and glycolysis which are aberrant in tumors, thereby providing other avenues for therapeutic intervention.
4. The invention provides a practical method for identifying clinically relevant tumor markers that may be useful in risk stratification, diagnosis, treatment monitoring, and nodal status, detection of cancer of the gingivo buccal complex, its recurrence and survival of the patient.

The invention claimed is:

1. A method for identifying co-expressed differentiator marker proteins comprising:
   a. providing a first sample from a cancer patient comprising malignant tissue from the gingivo-buccal area of the oral cavity of said cancer patient;
   b. providing a second sample comprising non malignant tissue from the gingivo-buccal area of the oral cavity of said cancer patient;
   c. micro-dissecting transformed epithelial cells from frozen sections of the malignant tissue and the non transformed epithelial layer from frozen sections of the non malignant tissue;
   d. separating proteins of lysates prepared from the micro-dissected transformed and non transformed epithelial cells from (c) by two dimensional gel electrophoresis and staining with silver;
   e. generating micro-dissected epithelial cell protein profiles from the samples in c) and d);
   f. comparing the micro-dissected epithelial cell protein profiles generated in step (e) and generating a short list of protein spots commonly expressed in both normal and transformed epithelium;
   g. punching out the short listed protein spots from a silver stained two dimensional gel of micro-dissected transformed epithelial cells;
   h. destaining and drying the protein spots and digesting obtained protein with trypsin;
   i. analyzing eluted dried peptides by mass spectroscopy to obtain identities of proteins;
   j. comparing the expression of each short-listed protein spot in non malignant and transformed epithelial cells to identity a set of co expressed differentiator marker proteins for the transformed epithelium from the group consisting of lactate dehydrogenase, alpha enolase, prohibitin, cathepsin D, apolipoprotein A-I, tumor protein translationally controlled-1, a stratifin (SFN) family protein, 14-3-3σ, tropomyosin and 14-3-3ζ (YWHAZ); and k. identifying key differentiator protein spots using Linear Discriminator Analysis.

2. A method as claimed in claim 1, wherein the key differentiator protein spots identified in step 14(k) respectively comprise the following proteins: 14-3-3σ, lactate dehydrogenase, and apolipoprotein A-I, and wherein upregulation of 14-3-3σ and downregulation of apolipoprotein is indicative of the presence of cancer.

3. A method for screening, detection, prognosis, or preparing a treatment regimen for cancer of gingivo-buccal complex in a patient, the method comprising the steps of:
(a) collecting a sample of epithelium tissue from the patient;
(b) a step for assaying the epithelium tissue in the sample to enable generation of an expression profile of a plurality of differentiator proteins comprising at least 14-3-3 σ, lactate dehydrogenase, and apolipoprotein A-I;
(c) generating the expression profile of the plurality of differentiator proteins;
(d) comparing the expression profile of the proteins generated in step (c) with a profile of the proteins from non-malignant tissue; and
(e) determining whether cancer may be present in the gingivo-buccal complex of the patient based on whether there is a difference in the expression profile of the proteins generated in step (c) and the profile of the proteins from non-malignant tissue.

4. The method according to claim 3, further comprising a step for conducting a biological assay or immunoassay for determining a level in the patient of a protein or proteins selected from the group consisting of 14-3-3 σ, lactate dehydrogenase, apolipoprotein A-I and a combination thereof.

5. The method according to claim 4, wherein the immunoassay is performed with an antibody against the protein or proteins.

6. The method according to claim 4, wherein the biological assay or immunoassay identities an upregulation of 14-3-3 σ and a downregulation of apolipoprotein and the method further comprises preparing a treatment regimen for treating the patient for cancer of the gingiva buccal complex based on the identification.

7. The method according to claim 3, wherein the plurality of differentiator proteins comprises a further protein or proteins in addition to 14-3-3 σ, lactate dehydrogenase, and apolipoprotein A-I.

8. The method according to claim 7, wherein the further protein or proteins are selected from the group consisting of alpha enolase, prohibitin, cathepsin D, tumor protein translationally controlled-1, a stratifin (SFN) family protein, tropomyosin and 14-3-3 ζ (YWHAZ).

9. The method according to claim 8, wherein the assaying comprises an immunoassay to determine a level of the plurality of differentiator proteins in the epithelium tissue of the sample.

10. The method according to claim 9, wherein the immunoassay is performed with an antibody against the protein or proteins.

11. A method for identifying potential therapeutic targets for cancer of gingivo-buccal complex in a patient, the method comprising the steps of:
(a) collecting a sample of epithelium tissue from the patient;
(b) assaying the epithelium tissue in the sample to enable generation of an expression profile of a plurality of differentiator proteins comprising at least 14-3-3 σ, lactate dehydrogenase, and apolipoprotein A-I;
(c) generating the expression profile of the plurality of differentiator proteins;
(d) comparing the expression profile of the differentiator proteins generated in step (c) with a profile of the proteins from non-malignant tissue and determining whether cancer may be present in the gingivo-buccal complex of the patient based on whether there is a difference in the expression profile of the proteins generated in step (c) and the profile of the proteins in the non-malignant tissue; and
(e) if the comparing in step (d) indicates a difference in the expression profile of the proteins generated in step (c) and the profile from non-malignant tissue, a step for conducting a biological assay or immunoassay for determining a level in the patient of one or more of the 14-3-3 σ, lactate dehydrogenase, and apolipoprotein A-I.

12. The method according to claim 11, comprising conducting an immunoassay for determining a level in the patient of a protein or proteins selected from the group consisting of 14-3-3 σ, lactate dehydrogenase, apolipoprotein A-I and a combination thereof.

13. The method according to claim 12, wherein the immunoassay is performed with an antibody against at least one of the differentiator proteins.

14. The method according to claim 11, wherein the biological assay or immunoassay in step (e) identifies an upregulation of 14-3-3 σ and a downregulation of apolipoprotein and the method further comprises preparing a treatment regimen for treating the patient for cancer of the gingiva buccal complex based on the identification.

* * * * *